United States Patent [19]

Kinoshita

[11] Patent Number: 4,548,197

[45] Date of Patent: Oct. 22, 1985

[54] AIR AND LIQUID SUPPLYING DEVICE FOR ENDOSCOPE

[75] Inventor: Kunio Kinoshita, Tokyo, Japan

[73] Assignee: Olympus Optical Co., Ltd., Tokyo, Japan

[21] Appl. No.: 591,999

[22] Filed: Mar. 21, 1984

[30] Foreign Application Priority Data

Mar. 22, 1983 [JP] Japan .................................. 58-47732
Mar. 31, 1983 [JP] Japan .................................. 58-56189
Mar. 31, 1983 [JP] Japan .................................. 58-56192

[51] Int. Cl.[4] .............................................. A61B 1/00
[52] U.S. Cl. ...................................................... 128/4
[58] Field of Search ....................... 128/4, 5, 6, 7, 8, 9, 128/10, 11

[56] References Cited

U.S. PATENT DOCUMENTS

| 4,261,343 | 4/1981 | Ouchi et al. | 128/4 |
| 4,311,134 | 1/1982 | Mitsui et al. | 128/6 |
| 4,325,362 | 4/1982 | Ouchi et al. | 128/4 |
| 4,489,712 | 12/1984 | Ohshimi | 128/6 |

FOREIGN PATENT DOCUMENTS

| 55394 | 7/1982 | European Pat. Off. | 128/4 |
| 81098 | 6/1983 | European Pat. Off. | |
| 2462897 | 2/1981 | France. | |

| 55-119251 | 3/1982 | Japan. |
| 5599512 | 7/1980 | Japan. |

Primary Examiner—William H. Grieb

[57] ABSTRACT

An air and liquid supplying device for an endoscope has a main body with a connecting portion and an air pump arranged in the main body. A first switch control valve is connected to an air supply channel and a liquid supply channel of the endoscope. A universal cord is connected at one end to a control section of the endoscope and at the other end to the connecting portion through a connector. A first air feed path extends from the first valve to the end of the connector through the universal cord. A liquid feed path extends from the first valve through the universal cord and communicates with a first liquid supply tank. The air pump is connected to the connecting portion through a second air feed path. A second liquid supply tank including second liquid is connected to the second air feed path. A second switch control valve is connected to the second air feed path to switch between the supply of air and the supply of the second liquid to the second air feed path. When the connector is not connected to the connecting portion, leakage of the second liquid through the connecting portion is prevented by a leakage preventing device.

14 Claims, 14 Drawing Figures

AIR AND LIQUID SUPPLYING DEVICE FOR ENDOSCOPE

BACKGROUND OF THE INVENTION

The present invention relates to an air and liquid supplying device for an endoscope and, more particularly, to an air and liquid supplying device which supplies a liquid to an air supply channel of an endoscope so as to clean it.

When an endoscope is used, a contaminant such as mucus may become attached to an observation window mounted at the distal end of an insertion section of the endoscope, so as to interfere with the field of view of the operator. In view of this problem, water is supplied to a nozzle at the distal end of the insertion section through a liquid supply channel of the endoscope to spray water on and clean the surface of the observation window. Then, air is supplied to the nozzle through an air supply channel to remove water from the observation window to allow accurate observation using the endoscope.

Infection by means of the endoscope also presents a problem. In order to resolve this, an insertion section of the endoscope is submerged in an infusion solution or disinfectant or an infusion solution is passed through a forceps channel to disinfect the channel. Furthermore, since water or an infusion solution can be similarly supplied to the liquid supply channel as well as the forceps channel, the liquid supply channel is also cleaned or disinfected.

When disinfection or sterilization of the overall endoscope is attempted, since a contaminant may flow back into the air supply channel through the nozzle, air supply channel cleaning must also be performed. However, due to the structure of the endoscope, cleaning/disinfection of the air supply channel is not easy. This leads to incomplete cleaning/disinfection of the air supply channel and consequent infection of patients.

SUMMARY OF THE INVENTION

The present invention has been made in consideration of this and has for its object to provide an air and liquid supplying device for an endoscope which has a simple structure, is capable of cleaning/disinfection of an air supply channel by supplying a liquid thereto, and does not allow accidental leakage of the liquid to the outside of the device when the endoscope is not in use.

According to an aspect of the present invention, there is provided an air and liquid supplying device for an endoscope, comprising: a main body with a connecting portion; an air pump arranged in the main body; a first liquid supply tank holding a first liquid therein; first switching means connected to an air supply channel and a liquid supply channel of the endoscope; communicating means having one end connected to a control section of the endoscope and the other end detachably connected to the connecting portion; connecting means having a first air feed path which has one end connected to said first switching means and the other end opening to the other end of said communicating means and which extends inside the communicating means, a second air feed path communicating the air pump and the connecting portion, a compressed air path branching from the first air feed path and communicating with the first liquid supply tank, and a liquid feed path communicating the first liquid supply tank and the first switching means; said first switching means being switchable between a first position at which the switching means communicates the first air feed path and the air supply channel to allow the supply of air from the air pump to the air supply channel and a second position at which the switching means communicates the liquid feed path with the liquid supply channel to allow the supply of the first liquid to the liquid supply channel; a second liquid supply tank holding a second liquid therein and connected to the second air feed path; second switching means, connected to the second air feed path at a position intermediate between the second liquid supply tank and the connecting portion, for switching between the supply of air and the supply of the second liquid to the second air feed path; and opening/closing means for communicating the first and second air feed paths when the other end of the communicating means is connected to the connecting portion and for preventing leakage of at least the second liquid through the second air feed path when the other end of the communicating means is not connected to the connecting portion.

In this device, the supply of air to the air supply channel and supply of the first liquid to the liquid supply channel can be switched by the first switching means. When the second switching means is switched, the second liquid can be supplied to the air supply channel through the first and second air feed paths. Thus, when an infusion solution is used as the second liquid, the air supply channel can be cleaned and disinfected. When the endoscope is not in use, that is, when the other end of the communicating means is not connected to the connecting portion, leakage of the second liquid through the second air feed path can be prevented by the opening/closing means.

BRIEF DESCRIPTION OF THE DRAWINGS

FIGS. 1 to 4 show an air and liquid supplying device according to a first embodiment of the present invention, in which FIG. 1 is a side view schematically showing the device together with an endoscope, FIGS. 2 and 3 are sectional views showing different parts of the device, and FIG. 4 is schematic sectional view of the endoscope;

DETAILED DESCRIPTION OF THE PREFERRED EMBODIMENTS

The preferred embodiments of the present invention will now be described in detail with reference to the accompanying drawings.

The first embodiment will first be described with reference to FIGS. 1 to 4.

Figure 1:
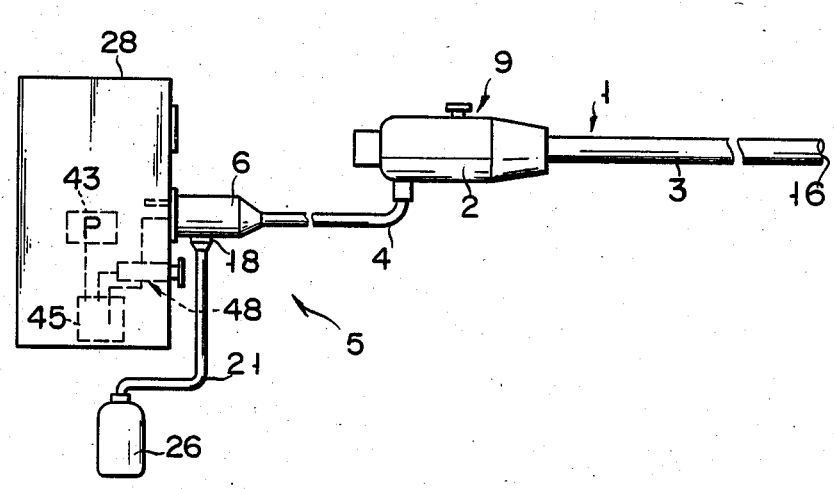

FIG. 1 shows an endoscope 1 and an air and liquid supplying device 5 connected thereto. The endoscope 1 has a control section 2 and an insertion section 3. An observation window (not shown) is arranged at the distal end of the insertion section 3. The air and liquid supplying device 5 has a main body 28 and a universal cord 4 which has one end connected to the control section 2 of the endoscope and the other end detachably connected to the main body 28 through a connector 6.

Figure 4:
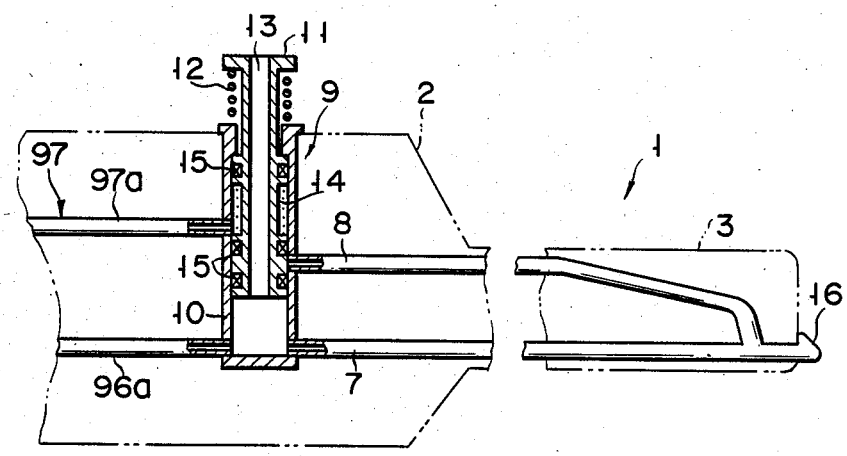

An air supply channel 7 and a liquid supply channel 8 are formed in the endoscope 1 to extend from the control section 2 to the distal end of the insertion section 3 (see FIG. 4). The downstream ends of the air supply channel 7 and the liquid supply channel 8, that is, the ends at the distal end of the insertion section 3, merge and communicate with a nozzle 16 formed at the distal end of the insertion section 3. The other end of each of the air supply channel 7 and the liquid supply channel 8 is connected to a first switch control valve 9 as a first switching means in the control section 2. A first air feed path 96a and a liquid feed path 97 are connected to the first switch control valve 9. The first air feed path 96a extends through the universal cord 4 and the connector 6. The liquid feed path 97 communicates with a first liquid supply tank 26 (to be described later) arranged outside the main body 28. The liquid feed path 97 has a first portion 97a which extends through the control section 2, the universal cord 4 and the connector 6, and a second portion 97b which communicates with the first liquid supply tank 26.

The first switch control valve 9 has a cylinder 10 mounted on the control section 2, a piston 11 slidably inserted inside the cylinder 10, and a spring 12 biasing the piston 11 in the direction to extend outside the cylinder 10, as shown in FIG. 4. The upstream end of the air supply channel 7 and the downstream end of the first air feed path 96a are connected to the peripheral wall at the lower end of the cylinder 10. The upstream end of the liquid supply channel 8 and the downstream end of the first portion 97a of the liquid feed path 97 are connected to the peripheral wall at the upper end of the cylinder 10. A leakage hole 13 extends axially in the piston 11, and an annular groove 14 is formed around the piston 11. When the piston 11 is biased by the spring 12 to extend outside the cylinder 10, as shown in FIG. 4, that is, when the piston 11 is at a first position, the air supply channel 7 and the air feed path 96a communicate with each other through the interior of the cylinder 10, and the piston 11 provides a seal between the liquid supply channel 8 and the liquid feed path 97. When the piston 11 is pressed inward against the biasing force of the spring 12, that is, when the piston 11 is at a second position, the piston 11 provides a seal between the air supply channel 7 and the air feed path 96a, while the liquid supply channel 8 and the liquid feed path 97 communicate each other through the annular groove 14 formed around the piston 11. An O-ring 15 is mounted on the piston 11 to provide a seal between the piston 11 and the cylinder 10.

The upstream end of the first air feed path 96a opens to the distal end face of a connecting mouthpiece 17 projecting from the end face of the connector 6. The upstream end of the first portion 97a of the liquid feed path 97 opens to a connecting portion 18 formed at a side surface of the connector 6. A compression path 19 branched from the air feed path 96a opens to the connecting portion 18. One end of a double pipe 21 is hermetically connected to the connecting portion 18 through a connecting mouthpiece 20. The double pipe 21 consists of an inner pipe 22 and an outer pipe 23. The inner pipe 22 defines the second portion 97b of the liquid feed path 97 therein. At the one end of the double pipe 21, the inner pipe 22 communicates with a central hole 24 formed in the connecting mouthpiece 20, and the outer pipe 23 communicates with a peripheral hole 25. When the connecting mouthpiece 20 is connected to the connecting portion 18, the inner pipe 22 communicates with the liquid feed path 97b through the central hole 24, and the outer pipe 23 communicates with the air feed path 96a through the peripheral holes 25. The other end of the double pipe 21 is hermetically connected to the first liquid supply tank 26 holding a first liquid L1 through a cap 27. At the other end of the double pipe 21, the outer pipe 23 communicates with the upper space inside the liquid supply tank 26, and the inner pipe 22 is submerged in the liquid L1.

Figure 2:
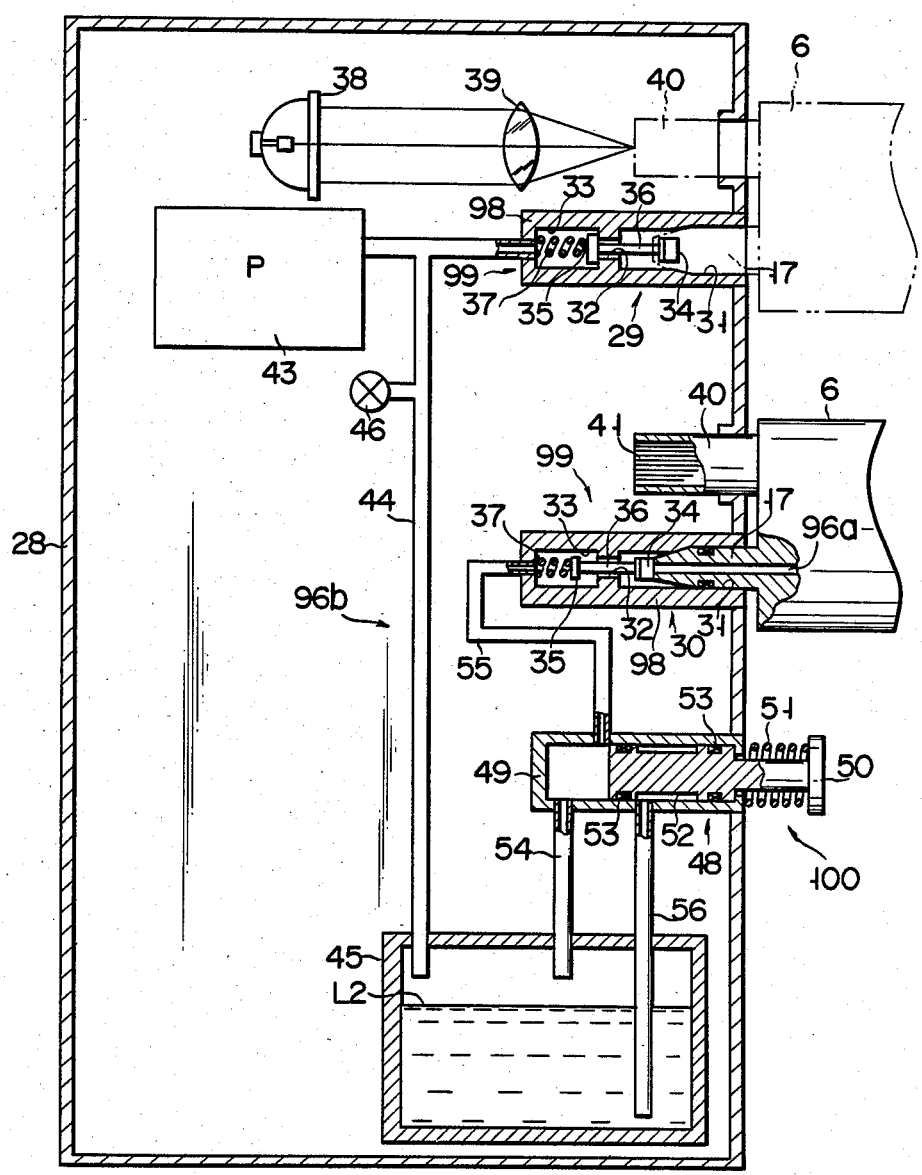
Figure 3:
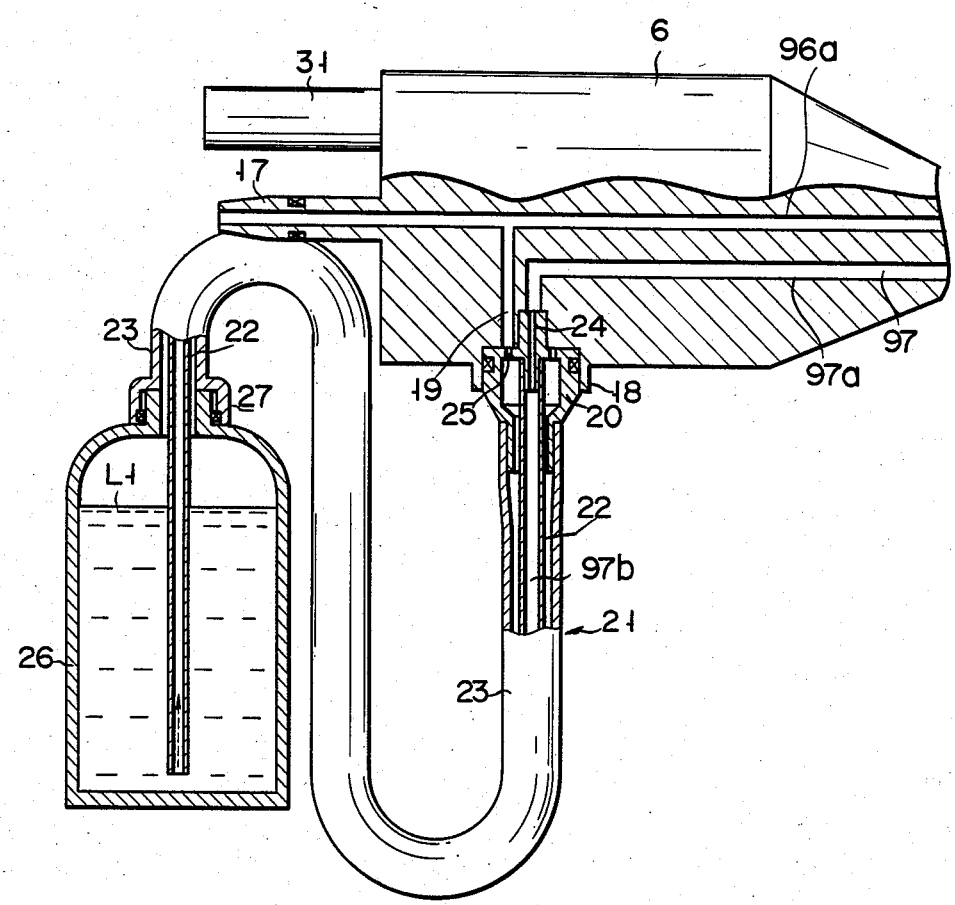

Referring to FIG. 2, a first connecting portion 29 for connecting the connector 6 and a second connecting portion 30 are mounted at a distance therebetween on the main body 28. Each connecting portion 29 or 30 has a receptacle 98 fixed to one side of the main body 28. An insertion hole 31, a through hole 32 and a storage chamber 33 are coaxially formed in each receptacle 98. One end of the insertion hole 31 opens to the one side wall of the main body 28 and the insertion hole 31 receives the connecting mouthpiece 17 of the connector 6. The storage chamber 33 communicates with the insertion hole 31 through the through hole 32. A valve stem 36 having a diameter smaller than that of the through hole 32 is slidably inserted therein. A press member 34 for abutting against the distal end of the connecting mouthpiece 17 of the connector 6 is fixed to that end of the valve stem 36 which is at the side of the insertion hole 31. A valve 35 for closing the through hole 32 is fixed to that end of the valve stem 36 which is at the side of the storage chamber 33. A spring 37 for biasing the valve 35 in the direction toward the insertion hole 31 is housed in the storage chamber 33. The spring 37 serves to normally close the through hole 32 by the valve 35. The first and second connection portions 29 and 30 respectively have through holes which are formed at the side wall of the main body 28 and can receive a light guide mouthpiece 40 projecting from the end face of the connector 6.

When the connector 6 is connected to the first or second connecting portion 29 or 30, the press member 34 is pressed by the connecting mouthpiece 17, and the valve stem 36 and the valve 35 are moved to the left against the biasing force of the spring 37. Then, the through hole 32 which has been closed by the valve 35 is opened. When the connector 6 is removed from the connecting portion, the valve 35 and the valve stem 36 are moved to the right by the spring 37, and the through hole 32 is closed by the valve 35. The valve 35, the valve stem 36, the press member 34, and the spring 37 constitute a leakage preventive means 99 of the present invention.

A light source 38 located near the first connecting portion 29 and a lens 39 for focusing light beam from the light source 38 are arranged in the main body 28. When the connector 6 is connected to the first connecting portion 29, the light beam focused by the lens 39 becomes incident on a light guide fiber 41 inside the light guide mouthpiece 40.

An air pump 43 and a second liquid supply tank 45 holding a second liquid L2 are also arranged in the main body 28. The discharge side of the air pump 43 communicates with the upper space of the second liquid supply tank 45 through an air supply pipe 44. A branch from the air supply pipe 44 communicates to the storage chamber 33 of the first connecting portion 29. A relief valve 46 is connected to the air supply pipe 44. A second switch control valve 48 as a second switching means 100 is interposed between the second connecting portion 30 and the second liquid supply tank 45. The switch control valve 48 has a cylinder 49, a piston 50 which is slidably inserted into this cylinder 49 and has one end projecting outward from one side of the main body 28, and a spring 51 which biases the piston 50 in a direction such that the piston 50 projects outward from the cylinder 49. An annular groove 52 is formed in the outer surface of the piston 50. An O-ring 53 for providing a hermetic seal between the piston 50 and the cylinder 49 is mounted on the piston 50. One end of a first connecting tube 54 communicates with the upper space of the second liquid supply tank 45 and the other end of the tube 54 is connected to the bottom portion of the wall of the cylinder 49. One end of a second connecting tube 55 communicates with the storage chamber 33 of the second connecting portion 30, and the other end of the tube 55 is connected to the top portion of the wall of the cylinder 49. One end of a lifting tube 56 is connected to that portion of the cylinder 49 which is closer to the open end thereof than are the connecting tubes 54 and 55. The other end of the lifting tube 56 is hermetically inserted into the second liquid supply tank 45 and is emersed in the liquid L2. The air supply pipe 44 and the first and second connecting tubes 54 and 55 define a second air feed path 96b. When the second switch control valve 48 is at a first position shown in FIG. 2, that is, when the piston 50 is biased by the spring 51 to protect outward, the first and second connecting tubes 54 and 55 communicate with each other through the internal space of the cylinder 49. When the piston 50 is pressed into a second position, the lifting tube 56 and the second connecting tube 55 communicate with each other through the annular groove 52 formed in the piston 50.

The operation of the air and liquid supplying device having the construction as described above will now be described.

When the endoscope 1 is used for general observation, the connector 6 is connected to the first connection portion 29, as indicated by the alternate long and two short dashed line in FIG. 2. Then, the press member 34 is pressed by the connecting mouthpiece 17 and the through hole 32 is opened. Then, the first air feed path 96a is connected to the air supply pipe 44 through the insertion hole 31, the through hole 32, and the storage chamber 33. While the first and second switch control valves 9 and 48 are not depressed, that is, while they are at the first positions, the light source 38 and the air pump 43 are actuated. Then, light beam from the light source 38 becomes incident on the light guide fiber 41. The air supplied from the air pump 43 enters the storage chamber 33 of the frist connecting portion 29 through the air supply pipe 44 and flows into the first air feed path 96a opening to the connecting mouthpiece 17 through the through hole 32 and the insertion hole 31. The air which has flowed into the air feed path 96a is released into the air from the leakage hole 13 formed in the piston 11 of the first switch control valve 9. Therefore, when the leakage hole 13 is closed with a finger, the air is sprayed through the nozzle 16 via the air supply channel 7. When a liquid is to be supplied to the liquid supply channel 8, the operator presses the piston 11 of the first switch control valve 9 to the second position. Then, the downstream end of the first air feed path 96a and the upstream end of the air supply channel 7 are sealed from each other, while the upstream end of the liquid supply channel 8 and the downstream end of the liquid feed path 97 communicate with each other. When the air feed path 96a is blocked, the air which has flowed into this air feed path flows into the first liquid supply tank 26 to compress the first liquid L1 therein through the compression path 19 in the connector 6 and the outer pipe 23 of the double pipe 21. The compressed liquid L1 flows into the first portion 97a of the liquid feed path 97 through the inner pipe 22 of the double pipe 21, into the liquid supply channel 8 through the annular groove 14 formed in the piston 11 of the first switch control valve 9, and flows out from the nozzle 16. In such air and liquid supplying operation, the air from the air pump 43 flows into the second liquid supply tank 45 and into the storage chamber 33 of the second connecting portion 30 through the cylinder 49 of the second switch control valve 48. However, since the connector 6 is not connected to the second connecting portion 30, the through hole 32 is closed by the valve 35. Accordingly, the air supplied from the air pump 43 will not leak from the second connecting portion 30. Even if the second switch control valve 48 is erroneously depressed to the second position, the second liquid L2 will not leak from the second connecting portion 30.

When the observation with the endoscope 1 is completed and the air supply channel 7 of the endoscope 1 is to be cleaned, the connector 6 is connected to the second connecting portion 30, as indicated by the solid line in FIG. 2. The piston 50 of the second switch control valve 48 is depressed to the second position to seal between the first and second connecting tubes 54 and 55 and to communicate the second connecting tube 55 and the lifting tube 56 through the annular groove 52 formed in the piston 50. Then, the second liquid L2 is compressed by the air supplied to the second liquid supply tank 45 from the air pump 43. The compressed liquid L2 flows into the storage chamber 33 of the second connecting portion 30. Then, the second liquid L2 flows into the first air feed path 96a of the connector 6 connected to the second connecting portion 30. When the leakage hole 13 of the piston 11 of the first switch control valve 9 is closed, the liquid L2 flows out from the nozzle 16 through the air supply channel 7. This flow of the second liquid L2 cleans the overall air feed path 96a and the air supply channel 7. If the second liquid L2 is an infusion solution, the air supply channel 7 is disinfected.

When the air supply channel 7 is disinfected in this manner and the biasing force acting on the piston 50 of the second switch control valve 48 is removed, the first and second connecting tubes 54 and 55 communicate with each other. Air then flows into the air supply channel 7 to drain the liquid L2 therein.

With the device having the above-mentioned construction, the liquid can be supplied to the air supply channel 7. Even when the liquid supply channel 7 is clogged, the air and liquid can be supplied through the air supply channel to allow normal endoscopic observation.

When the air supply channel 7 is to be cleaned and disinfected, the connector 6 is removed from the first connecting portion 29 and is connected to the second connecting portion 30. When the connector 6 is connected to the second connecting portion 30, light beam from the light source 38 is no longer incident on the light guide mouthpiece 40. Then, since no more light is irradiated from the endoscope 1, the insertion section 3 of the endoscope 1 cannot be inserted into a body cavity of a patient. In other words, while the insertion section 3 can be inserted into a body cavity of a patient, that is, the connector 6 is connected to the first connecting portion 29, even if the second switch control valve 48 is erroneously operated, the liquid L2 in the second air supply tank 45 will not be supplied to the body cavity of the patient. Especially when the second liquid L2 is an infusion solution, an accidental flow thereof into a body cavity of a patient will result in a fatal accident. However, the device of the present invention is free from such a problem.

Even if the air pump 43 is operated while the connector 6 is connected to neither of the first and second connecting portions 29 and 30, an increase in the pressure in the air supply pipe 44 is released by opening the relief valve 46. Thus, an overload operation and a short life of the air supply pump 43 will be prevented.

In the first embodiment described above, the first connecting tube 54 may be omitted. However, in this case, when the connector 6 is connected to the second connecting portion 30, the supply of only a liquid to the air supply channel 7 can be performed. Two air pumps (not shown) may be arranged in the main body 28. In this case, one pump is connected to the storage chamber 33 of the first connecting portion 29, while the other is connected to the second liquid supply tank 45.

Figure 5:
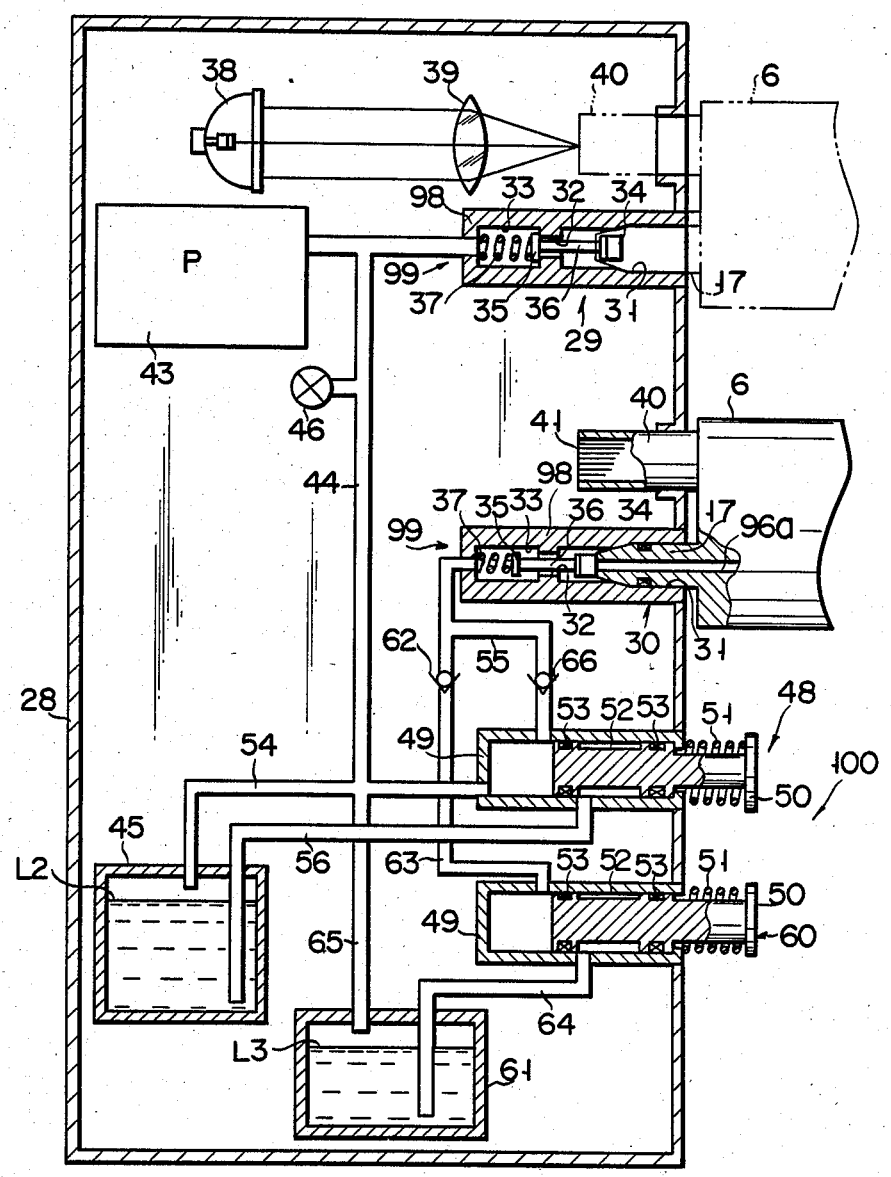
FIG. 5 is a sectional view of the main part of an air and liquid supplying device according to a second embodiment of the present invention.

FIG. 5 shows a second embodiment of the present invention. In this embodiment, a third switch control valve 60 have a same constraction with the second switch control valve 48 is arranged in the main body 28 as the second switching means 100. In addition, a third liquid supply tank 61 holding a third liquid L3 is arranged in the main body 28. A liquid supply tube 63 and a second lifting tube 64 are mounted in the third switch control valve 60. One end of the liquid supply tube 63 is connected to the wall of a cylinder 49, while the other end thereof is connected to the storage chamber 33 of the second connecting portion 30 through a first check valve 62. One end of the second lifting tube 64 is connected to the wall of the cylinder 49, while the other end thereof is submerged in the third liquid L3 held in the third liquid supply tank 61. An air supply branch pipe 65 branched from the air supply pipe 44 is connected to the third liquid supply tank 61 so as to communicate with the upper space therein. A second check valve 66 is mounted in the second connecting tube 55.

In the device of the second embodiment having the above-mentioned structure, when the connector 6 is connected to the second connecting portion 30, the operation of the second switch control valve 48 can allow flow of the liquid L2 in the second liquid supply tank 45 into the first air supply channel 7 of the endoscope 1 as in the case of the first embodiment. When the piston 50 of the second switch control valve 48 is depressed to the second position and a piston 50 of the third switch control valve 60 is depressed to the second position, the liquid supply tube 63 and the second lifting tube 64 communicate with each other through the annular groove 52 of the piston 50. Then, the third liquid L3 in a the third liquid supply tank 61 which has been compressed by the air from the air supply branch pipe 65 flows into the air supply channel 7. Thus, only the liquid L2 can be supplied to the air supply channel 7, or both the liquid L2 and the liquid L3 can be simultaneously supplied to the air supply channel 7. Accordingly, when the second liquid L2 is cleaning water and the third liquid L3 is a cleaning solution, the mixture of the liquids L2 and L3 is flowed into the air supply channel 7 and then only the liquid L2 is flowed therein. The air supply channel 7 can thus be cleaned with the mixture of the cleaning water and the cleaning solution and can then be cleaned with only the cleaning water. When the third liquid L3 is an infusion solution, this liquid L3 can be selected to disinfect the air supply channel 7. The air supply channel 7 can be simply washed with water. Since the check valves 66 and 62 are arranged for the second connecting tube 55 and the liquid supply tube 63, the liquid L3 in the third liquid tank 61 does not flow into the second liquid supply tank 45, and the liquid L2 of the second liquid supply tank 45 does not flow into the third liquid supply tank 61.

In this second embodiment, if the connector 6 is disconnected from the connecting portions 29 and 30, the through hole 32 is automatically closed by the valve 35. Thus, the air or liquid does not leak outside of the main body 28.

Figure 6:
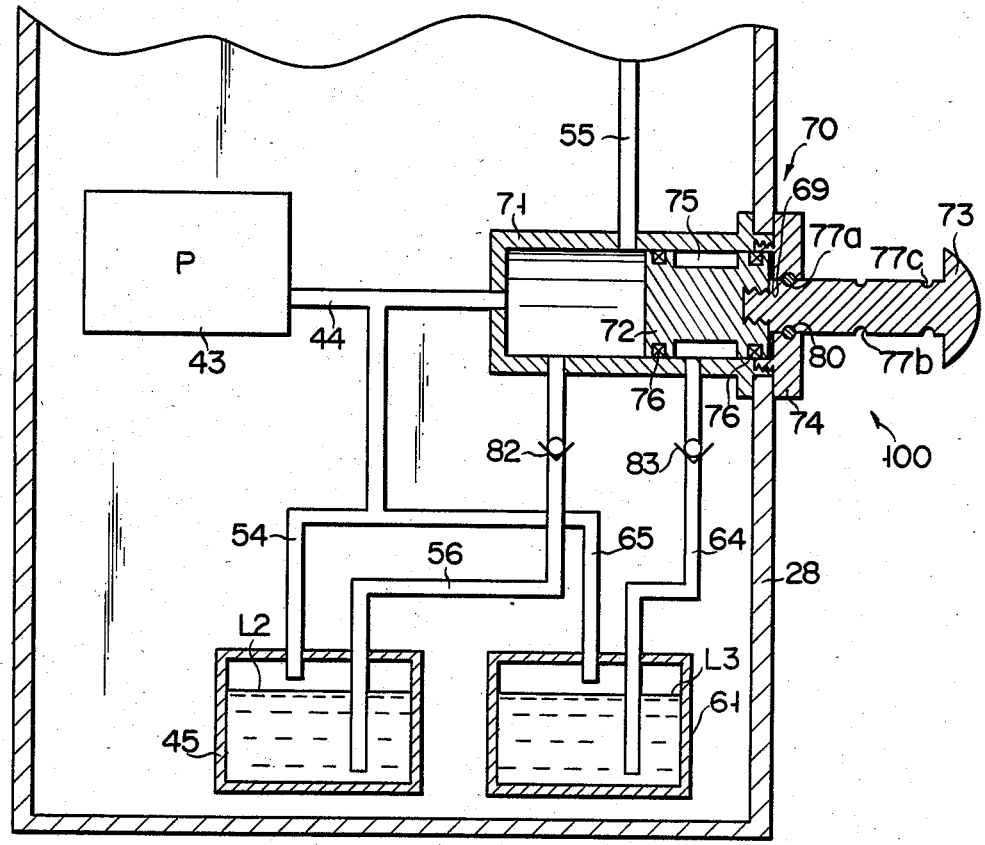
FIG. 6 is a sectional view of the main part of an air and liquid supplying device according to a third embodiment of the present invention.

FIG. 6 shows a third embodiment of the present invention. According to this embodiment, the second and third switch control valves 48 and 60 of the second embodiment are replaced by a fourth switch control valve 70 which allows a four-step operation as the second switching means 100. The fourth switch control valve 70 has a cylinder 71 fixed to the main body 28, a piston 72 slidably inserted in the cylinder 71, a control rod 73 connected to the piston 72 and projecting from the cylinder 71, and a cover 74 closing the opening of the cylinder 71. An annular groove 75 is formed in the outer surface of the piston 72, and an O-ring 76 for providing a hermetic seal between the piston 72 and the cylinder 71 is mounted on the piston 72. First to third annular engagement grooves 77a, 77b and 77c are formed in the outer surface of the control rod 73 at equal intervals along the axial direction of the rod 73. When the control rod 73 is pressed in the cylinder 71, the engagement grooves 77a to 77c sequentially and elastically engage with an O-ring 80 arranged on the inner surface of a through hole 79 of the cover 74. One end of the second connecting tube 55 communicates with the storage chamber 33 of the second connecting portion 30, while other end thereof is connected to a substantially intermediate position of the wall of the cylinder 71 along the axial direction thereof. One end of the lifting tube 56 is submerged in the liquid L2 in the second liquid supply tank 45, while the other end thereof is connected to the lower portion of the wall of the cylinder 71 through a first check valve 82. One end of the second lifting tube 64 is submerged in the liquid L3 in the third liquid supply tank 61, while the other end thereof is connected to the upper portion of the cylinder 71 through a second check valve 83. When the piston 72 is moved inside the cylinder 71 and is at the first position shown in FIG. 1, that is, when the first engagement groove 77a is engaged with the O-ring 80, the air supply pipe 44 and the connecting tube 55 communicate with each other through the inner space of the cylinder 71. When the piston 72 is pressed to the second position where the second engagement groove 77b of the control rod 73 engages with the O-ring 80, the connecting tube 55 and the second lifting tube 64 communicate with each other through the annular groove 75. When the piston 72 is further pressed to the third position where the third engagement groove 77c engages with the O-ring 80, the connecting tube 55 and the lifting tube 56 communicate with each other through the annular groove 75.

When the fourth switch control valve 70 of this construction is used, the liquid L3 in the third liquid supply tank 61 can be supplied to the air supply channel 7 by communicating the connecting tube 55 with the second lifting tube 64. When the connecting tube 55 and the lifting tube 56 communicate with each other, the liquid L2 in the second liquid supply tank 45 can be flowed into the air supply channel 7. In this manner, one of the liquids L2 and L3 can be selectively supplied to the air supply channel 7.

When the dimensions of the annular groove 75 are set in the third embodiment such that both the lifting tube 56 and the second lifting tube 64 are communicated with the connecting tube 55 when the piston 50 is pressed until the O-ring 80 engages with the third engagement groove 77c of the control rod 73, only the liquid L3 can be supplied to the air supply channel 7, or one of the liquids L2 and L3 can be selectively supplied thereto.

Figure 7:
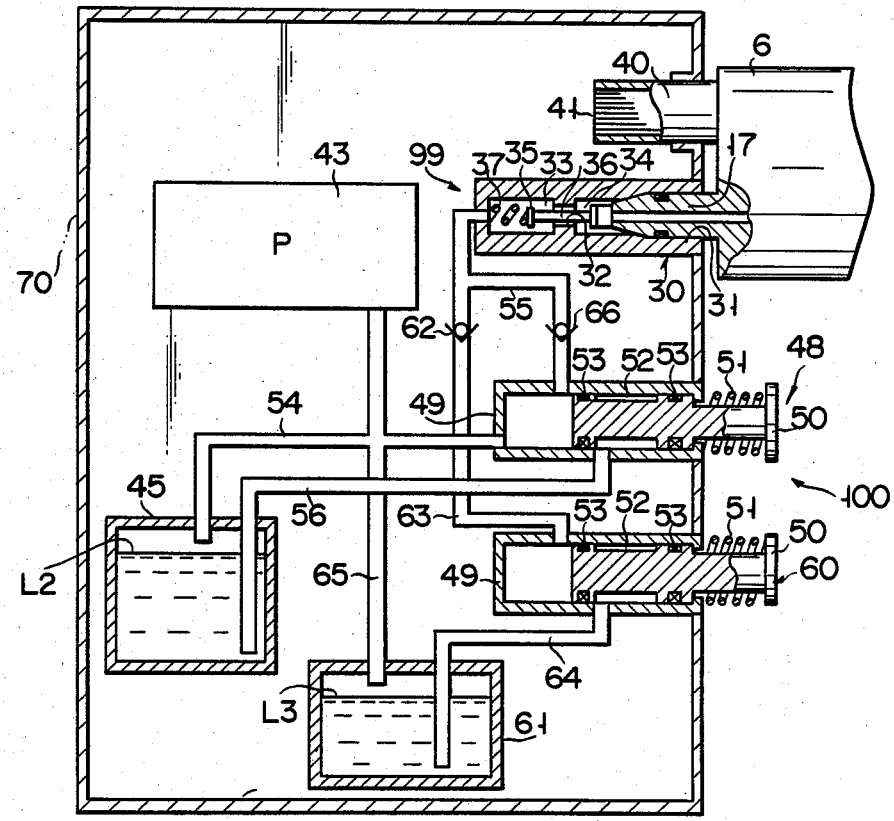
FIG. 7 is a sectional view of the main part of an air and liquid supplying device according to a fourth embodiment of the present invention.

FIG. 7 shows a fourth embodiment of the present invention. According to this embodiment, the first connecting portion 29 in the second embodiment is omitted, and the connector 6 is connected to the main body 28 only through the second connecting portion 30. A light source portion including the light source 38 and the lens 39 is omitted to provide an air and liquid supplying device unit having a single function and independent of the light source portion.

In the fourth embodiment, a liquid can be supplied to an air supply channel of an endoscope so as to allow easy and reliable cleaning and disinfection of the air supply channel. When the operator erroneously performs a water supply operation while the connector 6 is disconnected from the second connecting portion 30, the through hole 32 is automatically closed by the valve 35 and the liquid does not leak outside the main body 28 through the connecting portion 30, achieving a good hygienic condition. Since the connecting portion can be automatically sealed upon removal of the connector 6 from the connecting portion 30, a special operation is not required, and an accidental leakage is not provided. Thus, the device of the fourth embodiment of the present invention is clean and safe.

The means for preventing a leakage of a liquid from the connecting portion when the connector is removed from the connecting portion is not limited to those of the embodiments described above, and can be as shown in FIG. 8. According to this embodiment, the leakage preventing means 99 has a switch 102 as a photosensor which is arranged inside the main body 28 and near the second connecting portion 30. When the connector 6 is connected to the connecting portion 30, the main switch 102 is operated by the light guide mouthpiece 40 of the connector 6. The main switch 102 is arranged in that portion of the main body 28 which is not easily accesible. In this embodiment, the insertion hole 31 for receiving the connecting mouthpiece 17 of the connector 6 and a through hole 94 communicating with the insertion hole 31 are formed in the receptacle 98. The connecting tube 55 is connected to the through hole 94.

Figure 8:
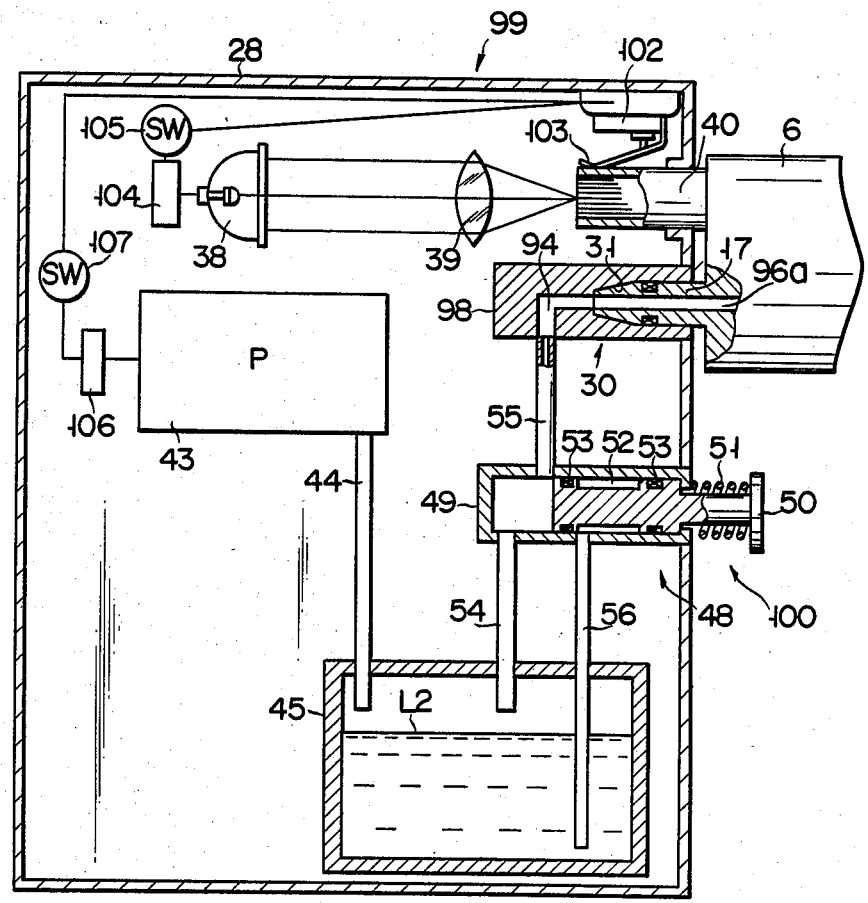
FIG. 8 is a sectional view of the main part of an air and liquid supplying device according to a fifth embodiment of the present invention.
Figure 9:
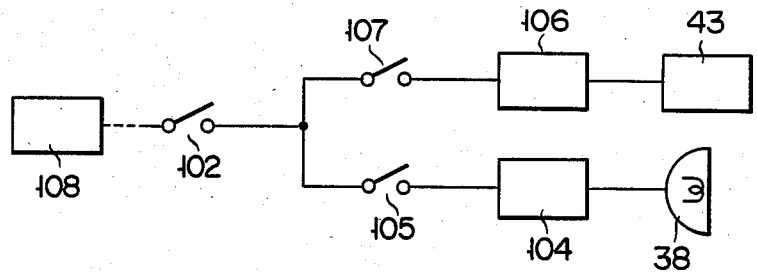
FIG. 9 is a circuit diagram of a control means.

The main switch 102 comprises a microswitch as shown in FIG. 8. An acutator 103 of the switch 102 is closed by the light guide mouthpiece 40 which projects when the connector 6 is connected to the second connecting portion 30. When the connector 6 is disconnected from the connecting portion 30, the actuator 103 is released, and the main switch 102 is opened. A lamp starter 104 of the light source 38 is connected to the main switch 102 through a lamp switch 105. A pump drive circuit 106 of the air supply pump 43 is connected to the main switch 102 through a pump auxiliary siwtch 107. These parts are wired in the manner as shown in FIG. 9. The elements at the side of the light source 38 and those at the side of the air pump 43 are connected to a power source 108 through the main switch 102, and are connected in parallel with each other. The main switch 102 is not closed unless the connector 6 is connected to the connecting portion 30. When the main switch 102 is not closed, the operation of the lamp switch 105 or the pump auxiliary switch 107 does not turn on the light source 38 or air pump 43. In this case, since the air pump 43 does not operate, the liquid supplying operation by the air pump 43, the second liquid supply tank 45 and so on is not enabled. Thus, the main switch 102 serves not to supply the air or liquid when the connector 6 is not connected to the first connecting portion 29, thereby preventing a leakage of the air or the second liquid L2 through the connecting portion 30.

According to the fifth embodiment described above, supply of air and liquid to the air supply channel of the endoscope can be easily performed as in the former embodiments. When the connector 6 is disconnected from the connecting portion 30, the main switch 102 is opened. Therefore, even if the lamp switch 105 and the pump auxiliary switch 107 are operated, no power is supplied to the light source 38 or air pump 43 which therefore do not operate. Thus, even if the second switch control valve 48 is operated to the liquid supply side, the liquid is not supplied. Thus, the liquid does not erroneously leak outside the main body 28 through the connecting portion 30. Furthermore, since the light source 38 is not turned on unless the endoscope 1 is connected, wasteful energization of the lamp is prevented. This provides a long life of the lamp and energy savings.

Since the main switch 102 is arranged at a position in the main body 28 which is not easily accessible, it is not accidentally operated and is safely protected.

Figure 10:
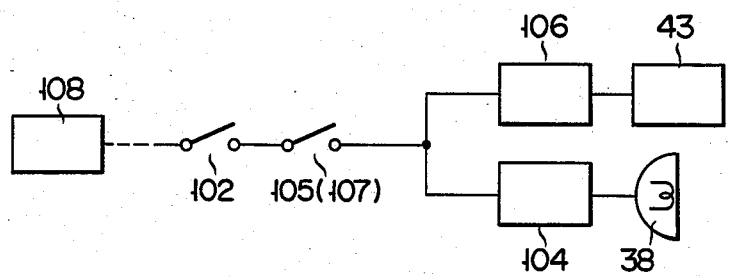
FIG. 10 is a circuit diagram of a control means according to a modification of the present invention.

The lamp switch 105 and the pump auxiliary switch 107 in the above embodiment may be synchronized. Furthermore, as shown in FIG. 10, a single switch may replace the switches 105 and 107. If these switches 105 and 107 are not particularly required, they may be omitted.

Figure 11:
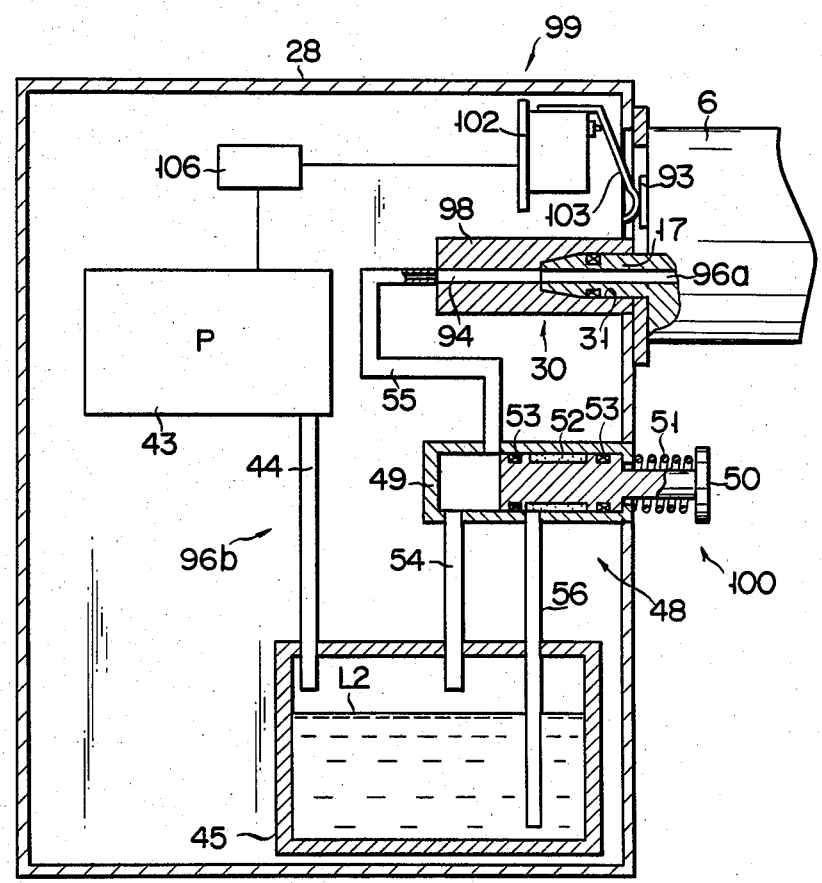
FIGS. 11 and 12 are a sectional view and a circuit diagram, respectively, of a control means according to a modification of the present invention.
Figure 12:
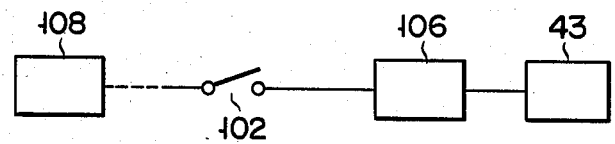

FIGS. 11 and 12 show a modification of the fifth embodiment of the present invention.

According to this modification, the light source unit including the light source 38, the lens 39 and so on is omitted. The main body 28 is an air and liquid supplying device unit separate from the light source unit. The actuator 103 extends to a position near the end of the receptacle 98 and is exposed from the main body 28. When the connector 6 is connected to the connecting portion 30, the actuator 103 of the main switch 102 is pressed by a projection 93 projecting from the end face of the connector. FIG. 12 shows the electric connections of the leakage preventive means 99. The actuator 103 slightly projects outward from the main body 28 and can be operated with a special tool or hand.

Figure 13:
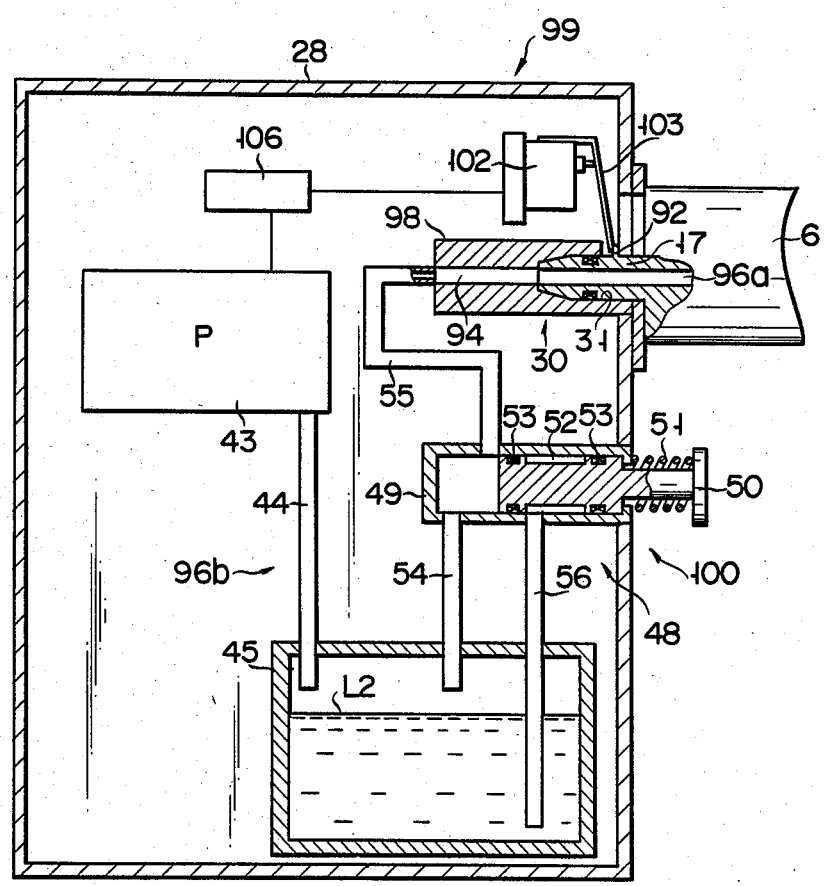
FIG. 13 is a sectional view of a control means according to another modification of the present invention.

FIG. 13 shows another modification of the fifth embodiment. According to this modification, the actuator 103 of the main switch 102 is operated with a control member 92 projecting from the connecting mouthpiece 17 of the connector 6. When the connector 6 is connected to the connecting portion 30, the connecting member 92 presses the actuator 103 to close the main switch 102. The actuator 103 is generally placed in the main body 28 and cannot be easily operated with hand or the like.

Figure 14:
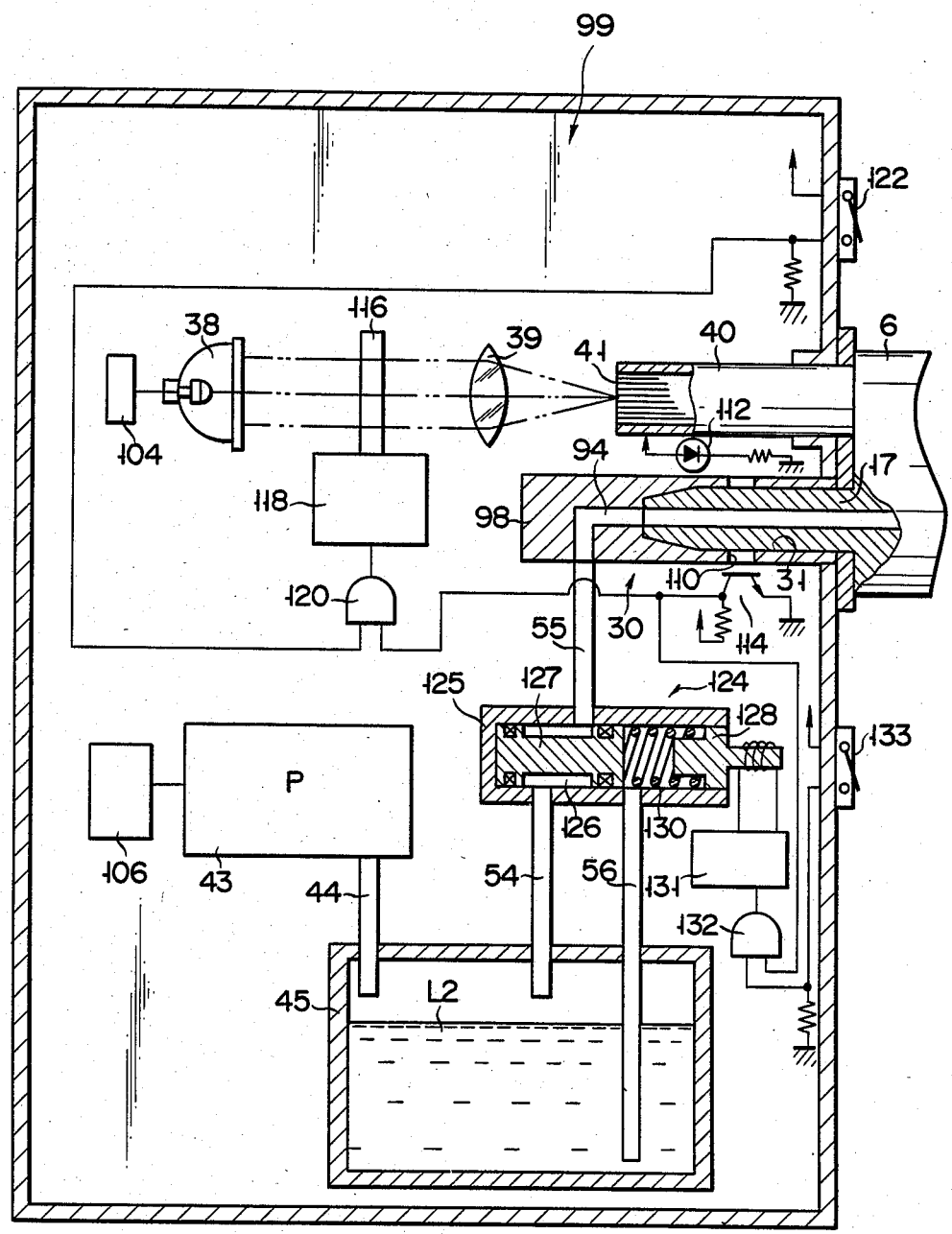
FIG. 14 is a sectional view of the main part of an air and liquid supplying device according to a sixth embodiment of the present invention.

FIG. 14 shows a sixth embodiment of the present invention. According to this embodiment, the leakage preventive means 99 comprises an LED, a photosensor or the like. The insertion hole 31 and a through hole 110 are formed in the receptacle 98 of the connecting portion 30. The through hole 110 crosses the insertion hole 31. An LED 112 is arranged above the through hole 110, while a photosensor 114 is arranged therebelow. A shutter 116 is interposed between the light source 38 and the lens 39. A drive circuit 118 of the shutter 116 is connected to the photosensor 114 through an AND circuit 120. One input terminal of the AND circuit 120 is connected to a lamp shutter drive switch 122 arranged at a side surface of the main body 28. In this embodiment, an electromagnetic valve 124 is arranged as the second switching means 100. The electromagnetic valve 124 has a cylinder 125, a piston 127 slidably arranged in the cylinder 124 and having an annular groove 126 on its outer surface, an electromagnet 128 fixed to one end of the cylinder 126, and a spring 130 which is arranged between the piston and the electromagnet and which biases the piston in the direction to move away from the electromagnet. The electromagnet 128 is connected to an AND circuit 132 through an electromagnetic valve drive circuit 131. One input terminal of the AND circuit 132 is connected to an electromagnetic valve drive switch 133 arranged at the side surface of the main body 28, and the other input terminal thereof is connected to the photosensor 114.

When a power source switch (not shown) arranged on the outer surface of the main body 28 is turned on, the lamp starter 104 and the pump drive circuit 106 are turned on to drive the light source 38 and the air pump 43 and to turn on the LED 112. When the connector 6 is not connected to the connecting portion 30, the light beam from the LED 112 becomes incident on the photosensor 114 through the through hole 110. Thus, the photosensor 114 is turned on, and the one input terminal of each of the AND circuits 120 and 132 goes to low level. Then, the output terminals of the AND circuits 120 and 132 go to low level and the shutter drive circuit 118 and the electromagnetic valve drive circuit 131 are not actuated. The shutter 116 is at a position between the light source 38 and the lens 39 to shield the light beam from the light source 38. For this reason, no light beam is emitted from the main body 28. The electromagnetic valve 124 is at the first position shown in FIG. 13, and the first and second connecting tubes 54 and 55 are connected through the annular groove 126 of the piston 127. The lifting tube 56 is closed by the piston 127.

When the connector 6 is connected to the connecting portion 30, light beam from the LED 112 is shielded by the connecting mouthpiece 17 and does not become incident on the photosensor 114. Thus, the one input terminal of each of the AND circuits 120 and 132 goes to high level. When the switch 122 is turned on, the other input terminal of the AND circuit 120 also goes to high level, and the output terminal thereof goes to high level. The shutter drive circuit 118 is actuated, and the shutter 116 is moved to a position where it does not shield light beam from the light source 38. Therefore, the light beam from the light source 38 becomes incident on the light guide fiber 41. When the switch 133 is turned on, the other input terminal of the AND circuit 132 also goes to high level, and the output terminal thereof goes to high level. Then, the electromagnetic valve drive circuit 131 is actuated to excite the electromagnet 128. The piston 127 is moved to the right against the biasing force of the spring 130 and is attracted by the electromagnet 128. The first connecting tube 54 is closed, and the lifting tube 56 and the second connecting tube 55 communicate with each other through the annular groove 126. As a result, the second liquid L2 is supplied to a communication path 94.

When the connector 6 is disconnected from the connecting portion 30 during the liquid supplying operation, light beam from the LED 112 becomes incident on the photosensor 114. Thus, the supply of liquid is stopped by the electromagnetic valve 124, and instead the air is supplied.

In this manner, in the sixth embodiment of the present invention, a liquid can be supplied to the air supply channel of an endoscope, and a leakage of the liquid L2 from the connecting portion can be prevented by the leakage preventive means when the connector is not connected to the connecting portion 30, as in the case of the former embodiments. Accordingly, the liquid does not leak from the main body 28 or is scattered around the device.

What is claimed is:

1. An air and liquid supplying device for an endoscope which includes a control section, an insertion section extending from the control section, and an air supply channel and a liquid supply channel extending from the control section to the distal end of the insertion section, said device comprising:
   a main body with a connecting portion;
   an air pump arranged in the main body;
   a first liquid supply tank holding a first liquid therein;
   first switching means connected to the air supply channel and the liquid supply channel;
   communicating means having one end connected to the control section and the other end detachably connected to the connecting portion;
   connecting means having a first air feed path which has one end connected to the first switching means and the other end opening to the other end of the communicating means and which extends inside the communicating means, a second air feed path connecting the air pump and the connecting portion, a compressed air path branching from the first air feed path and communicating with the first liquid supply tank, and a liquid feed path connecting the first liquid supply tank and the first switching means;

said first switching means being switchable between a first position at which the switching means communicates the first air feed path with the air supply channel to allow the supply of air from the air pump to the air supply channel and a second position at which the switching means communicates the liquid feed path with the liquid supply channel to allow the supply of the first liquid to the liquid supply channel;

a second liquid supply tank holding a second liquid therein and connected to the second air feed path;

second switching means, connected to the second air feed path at a position intermediate between the second liquid supply tank and the connecting portion, for switching between the supply of air and the supply of the second liquid to the second air feed path; and leakage preventive means for communicating the first and second air feed paths when the other end of the communicating means is connected to the connecting portion and for preventing leakage of at least the second liquid through the second air feed path when the other end of the communicating means is not connected to the connecting portion.

2. A device according to claim 1, wherein said connecting portion has a receptacle member fixed to the main body, an insertion hole which is formed in a receptacle member and has one end exposed to the outside of the main body, a storage chamber which is formed in the receptacle member and which communicates with the second air feed path, and a through hole which is formed in the receptacle member and communicates the insertion hole and the storage chamber; the communicating means has a universal cord which has one end connected to the control section and a connector connected to the other end of the universal cord, the connector having a connecting mouthpiece extending from the end face of the connector and detachably inserted in the insertion hole of the connecting portion; and the other end of the first air feed path opens to an extended end of the connecting port.

3. A device according to claim 2, wherein said leakage preventive means includes a valve stem which is slidably inserted in the through hole of the connecting portion, a valve which is mounted at that end of the valve stem which is at the side of the storage chamber and which is capable of closing the through hole, a press member which is mounted at that end of the valve stem which is at the side of the insertion hole and which is pressed by the connecting mouthpiece when the connecting mouthpiece is inserted in the insertion hole, and a biasing member which is arranged in the storage chamber and biases the valve in a direction to close the through hole.

4. A device according to claim 1, wherein said main body has another connecting portion to which the other end of the communicating means can be connected, and the second air feed path includes a branch path connected to the another connecting portion; and which further comprises another leakage preventive means for communicating the branch path and the first air feed path when the other end of the communicating means is connected to the another connecting portion and for closing the branch path when the other end of the communicating means is not connected to the another connecting portion.

5. A device according to claim 1, wherein said connecting portion has a receptacle member fixed to the main body, an insertion hole formed in the receptacle member and has one end exposed outside of the main body, and a communication path formed in the receptacle member and communicating with the insertion hole; the second air feed path is connected to the communication path; the communicating means has a universal cord having one end connected to the control section, and a connector connected to the other end of the universal cord, the connector having a connecting mouthpiece which extends from the end face thereof and which can be inserted into the insertion hole; and the other end of the first air feed path opens to an extending end of the connecting mouthpiece.

6. A device according to claim 5, wherein said leakage preventive means has a drive circuit connected to the air pump, and a switch which is connected to the drive circuit and arranged inside the main body, which energizes the drive circuit upon being turned on by the connector when the connector is connected to the connecting portion, and which deenergizes the drive circuit upon being turned off when the connector is not connected to the connecting portion.

7. A device according to claim 6, wherein said switch has an actuator which is actuated by the connecting mouthpiece of the connector.

8. A device according to claim 5, wherein said connecting portion has a through hole which is formed in the receptacle member and which crosses the insertion hole; the second switching means has an electromagnetic valve which can be switched between a first position at which the electromagnetic valve allows the supply of air to the second air feed path and a second position at which the electromagnetic valve allows the supply of the second liquid to the second air feed path; and the leakage preventive means has a light source which is arranged near one end of the through hole, and a sensor which is arranged near the other end of the through hole and which detects incident light from the light source through the through hole and switches the electromagnetic valve to the first position when the connector is not connected to the connecting portion and which detects a connection of the connector to the connecting portion and switches thereupon the electromagnetic valve to the second position.

9. A device according to claim 1, wherein said second switching means has a second switch control valve, and a lifting tube which has one end submerged in the second liquid in the second liquid supply tank and the other end connected to the second switch control valve; and the second switch control valve being switched between a first position at which the second switch cotnrol valve allows the supply of air from the air pump to the second air feed path and a second position at which the second switch control valve communicates the second air feed path with the lifting tube to allow the supply of the second liquid to the second air feed path.

10. A device according to claim 9, wherein said second switch control valve has a cylinder, a piston which is slidably arranged in the cylinder and which has an annular groove formed in an outer surface thereof, and biasing means for biasing the piston in a direction such that the piston projects outward from the cylinder; the second air feed path and the other end of the lifting tube communicate with the cylinder; and when the second switch control valve is at the first position, the piston closes the lifting tube and opens the second air feed path, and when the second switch control valve is at the second position, the piston closes an upstream end of the second air feed path and communicates the lifting tube and a downstream end of the second air feed path through the annular groove.

11. A device according to claim 1, wherein said first switching means has a first switch control valve; the first switch control valve having a cylinder which is connected to downstream ends of the first air feed path and the liquid supply path and upstream ends of the air supply channel and the liquid supply channel, a piston which is slidably arranged inside the cylinder and which has an annular groove formed on an outer surface thereof, and biasing means for biasing the piston in a direction such that the piston projecs outward from the cylinder; and the piston being switched between a first position at which the first switch control valve communicates the first air feed path and the air supply channel and a second position at which the piston closes the first air feed path and communicates the liquid feed path and the liquid supply channel through the annular groove.

12. A device according to claim 11, wherein said first switch control valve is arranged in the control section (2) of the endoscope.

13. A device according to claim 9, which further comprises a third liquid supply tank holding a third liquid therein; and wherein said second switching means includes an air supply branch pipe communicating the third liquid supply tank and the second air feed path, a third switch control valve, a lifting tube having one end connected to the third switch control valve and the other end submerged in the third liquid in the third liquid supply tank, a liquid supply tube having one end connected to the third switch control valve and the other end connected to the second air feed path at a position intermediate between the second switch control valve and the connecting portion; and the third switch control valve being switched between a first position at which the third switch control valve closes the lifting tube and a second position at which the third switch control valve communicates the lifting tube and the liquid supply tube to allow the supply of the third liquid to the second air feed path.

14. A device according to claim 1, which further comprises a third liquid supply tank holding a third liquid therein; and wherein said second switching means includes a switch control valve, a first lifting tube having one end connected to the switch control valve and the other end submerged in the second liquid in the second liquid supply tank, air supply branch tube communicating the third liquid supply tank and the second air feed path, and a second lifting tube having one end connected to the switch control valve and the other end submerged in the third liquid in the third liquid supply tank; and the switch control valve being switched among a first position at which the switch control valve closes the second lifting tube and opens the second air feed path, a second position at which the switch control valve closes an upstream end of the second air feed path and the first lifting tube and communicates a downstream end of the second air feed path and the second lifting tube to allow the supply of the third liquid to the second air feed path, and a third position at which the switch control valve closes the upstream end of the second air feed path and the second lifting tube and communicates the downstream end of the second air feed path and the first lifting tube to allow the supply of the second liquid to the second air feed path.

* * * * *